(12) United States Patent
Alzaga et al.

(10) Patent No.: US 11,488,313 B2
(45) Date of Patent: Nov. 1, 2022

(54) GENERATING A MOTION-COMPENSATED IMAGE OR VIDEO

(71) Applicant: Siemens Healthcare GmbH, Erlangen (DE)

(72) Inventors: Amilcar Alzaga, Nuremberg (DE); Günter Lauritsch, Nuremberg (DE); Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 227 days.

(21) Appl. No.: 16/777,539

(22) Filed: Jan. 30, 2020

(65) Prior Publication Data
US 2020/0250835 A1 Aug. 6, 2020

(30) Foreign Application Priority Data
Jan. 31, 2019 (DE) .......................... 102019201227.2

(51) Int. Cl.
*G06T 7/246* (2017.01)
*G06T 7/00* (2017.01)
*A61B 5/00* (2006.01)
*G06T 7/73* (2017.01)

(52) U.S. Cl.
CPC ............ *G06T 7/246* (2017.01); *A61B 5/7285* (2013.01); *G06T 7/0012* (2013.01); *G06T 7/73* (2017.01);
(Continued)

(58) Field of Classification Search
CPC ......... G06T 7/246; G06T 7/73; G06T 7/0012; G06T 2207/10081; G06T 2207/10072;
(Continued)

(56) References Cited

U.S. PATENT DOCUMENTS 7,343,195 B2 * 3/2008 Strommer ............ A61B 8/0833
600/424
9,913,693 B2 3/2018 Schulhauser
(Continued)

FOREIGN PATENT DOCUMENTS

CN 207123962 U 3/2018

OTHER PUBLICATIONS

Bandala, Manuel, and Malcolm Joyce. "Wireless inertial sensor for tumour motion tracking." Journal of Physics: Conference Series. vol. 76. No. 1. IOP Publishing, 2007.
(Continued)

*Primary Examiner* — Shefali D Goradia
(74) *Attorney, Agent, or Firm* — Lempia Summerfield Katz LLC (57) ABSTRACT

An imaging device and a method for generating a motion-compensated image or video are provided. The imaging device has a data acquisition facility for acquiring image data of a target object. The imaging device is configured to acquire, using a registration facility, a posture of an inertial measurement unit and, on the basis thereof, to carry out a registration between coordinate systems of the inertial measurement unit and the image data. The imaging device is further configured to acquire motion data from the inertial measurement unit arranged on the target object and, by processing the motion data, to generate the motion-compensated image or video.

15 Claims, 1 Drawing Sheet

(52) U.S. Cl.
CPC ........... *G06T 2207/10081* (2013.01); *G06T 2207/10121* (2013.01)

(58) Field of Classification Search
CPC . G06T 2207/10121; G06T 2207/10116; A61B 5/7285
See application file for complete search history.

(56) References Cited

U.S. PATENT DOCUMENTS

| | | | |
|---|---|---|---|
| 2010/0168559 A1 | 7/2010 | Tegg | |
| 2011/0054308 A1* | 3/2011 | Cohen ............... | A61B 5/06 600/424 |
| 2011/0158488 A1* | 6/2011 | Cohen ............... | A61B 6/527 382/128 |
| 2011/0160571 A1* | 6/2011 | Cohen ............... | A61B 5/066 600/424 |
| 2013/0172730 A1* | 7/2013 | Cohen ............... | A61B 6/12 600/424 |
| 2014/0226891 A1 | 8/2014 | Kunze | |
| 2016/0278746 A1* | 9/2016 | Hancu ............... | A61B 10/0266 |
| 2017/0215969 A1 | 8/2017 | Zhai | |
| 2017/0273665 A1 | 9/2017 | Kapoor | |
| 2018/0055576 A1 | 3/2018 | Koyrakh | |
| 2020/0219254 A1* | 7/2020 | Regensburger ....... | G06T 7/0012 |

OTHER PUBLICATIONS

Farahmand, Farid, Kevin O. Khadivi, and Joel JPC Rodrigues. "Improving radiation oncology using a low-cost wireless accelerometer." 34th Conference on Local Computer Networks. IEEE, 2009. pp. 724-729.

Fischer, Peter, Thomas Pohl, and Joachim Hornegger. "Real-time respiratory signal extraction from x-ray sequences using incremental manifold learning." 11th International Symposium on Biomedical Imaging (ISBI). IEEE, 2014. pp. 1-4.

German Office Action for German Application No. 10 2019 201 227.2 dated Dec. 3, 2019.

Grangeat, Pierre, et al. "Theoretical framework for a dynamic cone-beam reconstruction algorithm based on a dynamic particle model." Physics in Medicine & Biology 47.15 (2002): 2611.

Heimann, Tobias, et al. "Real-time ultrasound transducer localization in fluoroscopy images by transfer learning from synthetic training data." Medical image analysis 18.8 (2014): 1320-1328.

Rit, Simon, et al. "On-the-fly motion-compensated cone-beam CT using an a priori model of the respiratory motion." Medical physics 36.6Part1 (2009): 2283-2296.

Rohkohl, Christopher, et al. "Interventional 4D motion estimation and reconstruction of cardiac vasculature without motion periodicity assumption." Medical Image Analysis 14.5 (2010): 687-694.

Schafer, Dirk, et al. "Motion-compensated and gated cone beam filtered back-projection for 3-D rotational X-ray angiography." IEEE transactions on medical imaging 25.7 (2006): 898-906.

Sindel, Aline, et al. "Respiratory motion compensation for c-arm CT liver imaging." Bildverarbeitung für die Medizin 2015. Springer Vieweg, Berlin, Heidelberg, 2015. pp. 221-222.

Syben, Christopher, et al. "Joint calibration and motion estimation in weight-bearing cone-beam CT of the knee joint using fiducial markers." 14th International Symposium on Biomedical Imaging. IEEE, 2017. pp. 494-497.

* cited by examiner

GENERATING A MOTION-COMPENSATED IMAGE OR VIDEO

This application claims the benefit of DE 10 2019 201 227.2, filed Jan. 31, 2019, which is hereby incorporated by reference in its entirety.

BACKGROUND

The present embodiments relate to generating a motion-compensated image or video, Imaging devices and methods are widespread nowadays in many technical fields and application areas (e.g., in the medical environment for imaging target objects or examination objects, such as patients or tissue samples or the like). With regard to an image quality of the finally resulting images or videos, it may thereby be problematic if the target object or examination object moves while the target object or examination object is imaged or between two imaging time points. Such movements (e.g., respiratory motions of a patient) may, for example, lead to a computed tomography (CT) volume image reconstructed from a plurality of projection images, recorded at different positions or postures of the patient, appearing blurred, so that anatomical structures are not recognizable, and the CT volume image is therefore diagnostically unusable.

A plurality of approaches already exist in order to counteract this problem.

Thus, for example, for the avoidance of a motion in patients under general anesthetic, a mechanical ventilation may be switched off for a while, or a patient without anesthesia may be instructed to hold their breath during the recordings. In the publication "Interventional 4D motion estimation and reconstruction of cardiac vasculature without motion periodicity assumption" by C. Rohkohl et al. in Medical Image Analysis 14 (2010), pages 687-694, an image-based approach is proposed. A reference image, in which a vascular system is visible, is reconstructed. Subsequently, parameters of a motion model are estimated by optimizing a target function. The target function is aimed at maximizing an overall intensity of the reference image and a motion-compensated FDK reconstruction.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved capability for motion compensation for an improved image quality is provided.

An embodiment of an imaging device serves and is therefore configured for generating a motion-compensated image or video of a target object. Thus, an individual image or a plurality of images may be generated, where a temporal sequence of a plurality of images may form the video. The image or the images may be 2D images or 3D images (e.g., a CT volume image). The target object may be a patient or a part of a patient (e.g., an abdominal region, an organ, a vascular tree, or a tissue sample). In principle, however, the target object may ultimately be any desired object that is accessible to imaging by the imaging device.

The imaging device has a data acquisition facility for acquiring image data of the target object. For example, X-ray image data may be acquired as the image data. The imaging device may further include a reconstruction facility for generating or reconstructing at least one X-ray image of the target object from the X-ray image data. The generated or reconstructed X-ray image may then already be the motion-compensated image. Equally, however, the motion-compensated image may be generated, for example, from the X-ray image or, in general, from the image data or may include the X-ray image, the image data, or an image generated from the image data, or may be combined therewith, for example, for an augmented reality representation. Equally, however, for example, optical image data such as, for example, endoscope image data or endoscope video data, ultrasonic data, magnetic resonance data, or the like may be acquired as the image data. According to the present embodiments, the image device is configured to acquire, by a registration facility, a posture of an inertial measurement unit (IMU) and, on the basis thereof, to carry out a registration between coordinate systems of the inertial measurement unit and the image data or an image generated therefrom.

The coordinate system of the inertial measurement unit is the coordinate system in which the inertial measurement unit records measurement or sensor data. The coordinate system of the image data of the image generated therefrom, however, is the coordinate system in which the image data is or has been recorded. In the case of X-ray images, this may thus be, for example, a coordinate system of a radiation source and a detector of the imaging device and/or of a room in which the imaging device or the radiation source and the detector are arranged.

According to one or more of the present embodiments, the imaging device is configured to acquire motion data from the inertial measurement unit arranged on the target object and, by processing this motion data, to generate the motion-compensated image or video. The motion data describes a translational and/or rotational motion of the inertial measurement unit, for example, in the form of acceleration data (e.g., an intensity and/or a direction with which or in which the inertial measurement unit is or has been moved or accelerated). Since it is intended that the inertial measurement unit records the motion data while the image data is recorded (e.g., while the target object is imaged for recording the image data) and since the inertial measurement unit is arranged, for example, on the target object, the motion data obtained by the inertial measurement unit may be used as the basis or reference for the motion compensation. The motion data of the inertial measurement unit thus defines a motion of the target object.

Since the motion of the target object is thus measured by the inertial measurement unit, no estimation or indirect methods for determining the motion of the target object is necessary. For example, as distinct from the prior art, no additional recording of a reference image of the target object for the motion compensation, or motion compensation is necessary, so that with the present embodiments, a radiation burden on the target object may be reduced as compared with the prior art.

The inertial measurement unit may thus specify the motion or a motion field of the target object during the recording of the image data in the form of the motion data. For the actual motion compensation based on this motion data, known procedures or methods may then be used. For example, position data of the target object derived from the motion data may be added to the image data or subtracted therefrom in order to effectively eliminate (e.g., compensate for) the motion of the target object in the coordinate system of the image data. This may be carried out separately for each frame (e.g., for each individual image, such as each X-ray image or projection image of the image data), whereby a blurring or unsharpness in an image generated therefrom (e.g., a 3D or volume image) may be prevented or reduced. For this, both the image data and also the motion data may be provided with respective time signatures that enable a temporal allocation between the image data and the motion data.

The imaging device may be, for example, a computed tomography device, a magnetic resonance tomography device, an ultrasonic device, an optical imaging device (e.g., a camera or an endoscope for recording optical image data or the like with an integrated data processing facility), a system made from such a device and a data processing facility directly or indirectly connected thereto, or a data processing facility. In the first two cases, the acquisition of the image data may include, for example, a recording or scanning (e.g., the actual imaging of the target object). For example, if the imaging device is a data processing facility, the acquisition of the image data may include or be a reception or retrieval of the image data via a corresponding data interface of the data processing facility. The facilities of the imaging device (e.g., the data acquisition facility, if relevant, the reconstruction facility and the registration facility, and, if relevant, a superimposition facility) may be or include corresponding program and/or hardware modules of the data processing facility or of the imaging device. Thereby, some or all of the facilities may be combined or integrated with one another.

With the present embodiments, during imaging (e.g., during the recording or acquisition of the image data of the target object), movements of the target object may be measured and tracked with particular accuracy and detail. Thus, the present embodiments also provide the possibility of generating motion-compensated images or videos with improved image quality and also of movable or moving target objects or parts thereof, for example, of movable or moving organs of a patient, whereby, for example, no active or passive breathing control or guidance of the respiratory motion is necessary.

In order to provide that from the motion data obtained by the inertial measurement unit, conclusions may be reliably drawn regarding the motion of the target object, the inertial measurement unit may be arranged with corresponding directness (e.g., directly) or indirectness (e.g., indirectly) on the target object. This provides that the inertial measurement unit may therefore be situated in a positional relationship to the target object that is pre-determined and therefore known or specified as a parameter.

Depending on the individual case, the inertial measurement unit may simply be, for example, placed onto the target object from outside, and equally, the present embodiments may be usefully applied not only to human or animal bodies.

The relative positional relationship between the target object and the inertial measurement unit may be derived from the image data, for example, by a distance measurement. Similarly to the acquisition of the image data, the acquisition of the motion data may include or be a reception or retrieval of this motion data by the imaging device from the inertial measurement unit or an intermediate storage facility. The acquisition of the image data and/or the acquisition of the motion data may thus take place at a different time point from the generation of the motion-compensated image.

The use of the inertial measurement unit for the acquisition or recording of the motion data is advantageous, for example, as compared with a use of conventional markers that are more visible in a respective imaging modality (e.g., more X-ray visible) since, in contrast to the markers for the inertial measurement unit, is the inertial measurement unit does not have to be permanently visible to a corresponding recording device during the recording of the image data (e.g., the imaging device, the data acquisition facility thereof, or a camera, or the like).

In an embodiment, the imaging device is configured to acquire a 3D CT data record as the image data. This 3D CT data record may include, for example, a plurality of projection images recorded from different angles or angulations. The imaging device is then configured to acquire the motion data of the inertial measurement unit simultaneously with the image data and, as the motion-compensated image, to reconstruct, from the 3D CT data record and the motion data, a motion-compensated 3D image (e.g., a CT volume image of the target object).

In other words, the imaging device is thus configured, based on the motion data, to determine the motion of the target object during the acquisition or recording of the image data or to use or interpret the motion data as motion data for the target object. The raw data or individual data for the 3D CT data record (e.g., the individual X-ray or projection images) usually cannot be recorded instantaneously simultaneously according to the present state of the art; rather, for this, a certain recording time or recording duration is needed. During this recording time or recording duration, the target object may move, which leads either to an unsharpness (e.g., a reduction in the image quality) in an ultimately reconstructed CT volume image or a compensation with corresponding measures.

Patients who are imaged as the target object are often in a state that does not permit or enable the patients to exercise sufficiently controlled breath-holding or even sufficient breathing over a plurality of respiratory cycles. This may be the case due, for example, to injuries or sedation. In such cases, a sufficiently even respiration may not be assumed in order, based on a previously recorded respiratory cycle, to enable a reliable and accurate motion compensation. The use of the inertial measurement unit then forms a particularly simple, reliable, flexibly usable and, for the patient, low-burden possibility for obtaining motion data as the starting point or basis for the motion compensation.

In a further embodiment, the imaging device is configured to generate, from the motion data of the inertial measurement unit, as the motion-compensated image, a motion-compensated overlay image, and to overlay the motion-compensated overlay image on the image data or the at least one image generated therefrom (e.g., an X-ray, CT, MR, ultrasonic, or camera image).

An exemplary application case for this embodiment may be, for example, that a physician wishes to move a catheter through a vascular tree to a target location in an anatomy (e.g., in the patient). It is then possible that as the image data or the image generated therefrom, fluoroscopy data or images are recorded, on or in which, however, substantially only the X-ray visible catheter itself is visible or recognizable, whereas an anatomical background is not, or is only relatively weakly, contrasted. For example, if the vascular tree has no branch at a current position of the catheter and/or if the catheter is withdrawn from the vascular tree, it may be sufficient for a successful intervention to visualize only the motion of the catheter itself in order to assist the physician during a navigation of the catheter through the vascular tree. The catheter or a respective current position of the inertial measurement unit may then be moved as a virtual overlay image over a respectively last recorded X-ray image (e.g., the most currently available X-ray image).

For this, the inertial measurement unit may be arranged, for example, in or on the catheter. The overlay image may then be moved according to motion data, whereby the current position of the catheter, or a corresponding other instrument, may be represented realistically (e.g., true to reality) in the motion-compensated image.

In comparison with conventional image-based methods, the motion compensation of the overlay image may take place at an update or image rate that is greater than an image or frame rate (e.g., the recording rate or recording frequency with which the image data, such as the fluoroscopic images, is recorded). The overlay image may then therefore move more fluidly than the image lying therebehind. In this way, for example, a dose and therefore a burden on the patient may be reduced or saved, since for a fluid or fluidly represented overlay image, correspondingly high image rates are no longer required. This may be advantageous in the case of X-ray image data. Through the use of the inertial measurement unit, therefore, a robust motion-compensated overlay image may be generated. The robust motion-compensated overlay image functions even at a reduced image rate, and thus possibly a correspondingly reduced dose, at poor contrast and/or irregular breathing motions (e.g., enables a realistic position representation).

Equally, for example, the overlay image may be overlaid on an endoscopic image or endoscopic video recorded as the image data. Using the present embodiments, based on the motion data of the inertial measurement unit, the overlay image may then be motion-compensated or may be represented motion-compensated. Thus, it can be provided that the overlay image is motion-compensated and is thus also always consistent during a motion of the target object and is overlaid on the endoscopic video in the correct spatial relationship thereto. For example, for this purpose, the inertial measurement unit may be anchored to the target object during an intervention (e.g., during a liver operation, cemented to a surface of the liver). The inertial measurement unit then moves together with the target object (e.g., together with the liver) and thereby measures the corresponding motion.

In a development of the present embodiments, the imaging device is configured, during acquisition of the motion data, to automatically reduce a recording rate at which the imaging device acquires the image data to or by a pre-determined value. In other words, the X-ray image data may thus be recorded, for example, at the reduced image or recording rate for as long as the motion data is acquired (e.g., is updated or is present, in real time). As soon as motion data or current motion data is no longer acquired or present and/or as soon as another pre-determined condition is fulfilled, the recording rate may be increased again, for example, automatically. The overlay image may thus be updated at a higher image rate or frequency than the image data or the image generated therefrom, where the respectively most current overlay image is overlaid on the respectively most current available image data or the respectively last image created therefrom.

Due to the automatic control of the recording rate, a dosage burden for the target object may be safely and reliably reduced. In addition, for example, the respective physician or a respective operating personnel of the imaging device may be relieved of a manual adaptation of the recording rate, whereby more attention may be paid to the target object (e.g., therefore to the patient), so that there is a greater probability of a treatment success and a probability of an error or an error frequency in a respective operation or a respective intervention may be reduced.

In a development of the present embodiments, the imaging device is configured to acquire image data with regular repetition and therefrom, if relevant, to generate a respectively updated image. Based on a contrast of the image data or of the images generated therefrom, a contrast medium injection may automatically be detected. For this purpose, for example, a threshold value and/or a particular speed of change or a scope of change of the contrast may be pre-determined as an indication of the contrast medium injection. The imaging device is then configured, on detecting a contrast medium injection, to increase the recording rate for the image data to or by a pre-determined value. typically, a contrast medium injection will take place in a moment or time period that is particularly important or decisive or critical for a successful intervention, a successful treatment, or a successful diagnosis. In such a moment or time period, the increased recording rate may then supply or enable more detail information (e.g., an improved or more exact understanding of a current situation), whereby the success may be further supported. It is advantageous that by the automatically controlled increasing of the recording rate, respective operating personnel (e.g., a treating physician) is relieved thereof at the critical moment.

The imaging device may be configured to reduce the recording rate again automatically by the pre-determined value or a further pre-determined value if the contrast has fallen to or by a pre-determined value and/or if since the contrast medium injection, a pre-determined timespan or time duration has passed. In other words, the recording rate may thus be adjusted or set (e.g., increased or reduced automatically, adaptively, and dynamically) according to the situation and need. By this, an optimal compromise may be achieved with regard, firstly, to a treatment or diagnosis success and, secondly, to the smallest possible burden on the target object. Thereby, for particular situations or requirements, it may be left to the respective physician or operating personnel to automatically overdrive the automatic control or adaptation of the recording rate, whereby an improved flexibility and possibly an optimized treatment or diagnostic result may be achieved particularly reliably.

In a further embodiment, the medical imaging device includes a movably mounted support equipped with a drive for positioning the target object. The support, which may be, for example, a patient support or a patient table, is thus movable or displaceable by the drive. The imaging device is then configured, in the event of a motion of the support in different spatial directions, to acquire both this motion and also the motion data obtained by the inertial measurement unit, and to determine the posture or an orientation of the inertial measurement unit to put the motion and the motion data in relation to one another (e.g., to combine, equalize, or correlate the motion and the motion data). In one embodiment, the image data may also be taken into account or placed in relationship in order to be able to determine the posture (e.g., the orientation and a location or position of the inertial measurement unit, in the coordinate system of the image data) particularly reliably and accurately.

A fundamental problem in the use of the inertial measurement unit for recording the motion data is that the inertial measurement unit typically only supplies relative motion data in its own coordinate system, and, accordingly, an absolute motion curve in an external coordinate system (e.g., an earthbound coordinate system or the coordinate system of the imaging device or of the image data or the image created therefrom) is initially not defined or known. This problem is solved, however, by the registration provided.

In the present case, therefore, a spatial position and/or orientation of the inertial measurement unit (e.g., before the start of a recording of the image data) may be determined in relation to the external coordinate system (e.g., in relation to the imaging device). Since the support is part of the imaging device, a spatial position and orientation of the support in the coordinate system of the imaging device (e.g., relative to a pre-determined coordinate origin and/or relative to the radiation source and the detector of the imaging device) is always known (e.g., specified or easily readable). For this purpose, for example, a status signal of the drive or of a corresponding sensor may be read out or evaluated, or starting from a pre-determined start position, the position and orientation of the support may be tracked according to respective control commands output to the drive for moving the support. This may involve both control commands generated automatically (e.g., by a control facility or a control device of the imaging device) as well as such control commands as are generated by a manual operation action of a respective user or operating personnel.

Through the simultaneous acquisition of the motion of the support and the motion data (e.g., a corresponding motion) of the inertial measurement unit while the inertial measurement unit is situated in a pre-determined (e.g., constant relative spatial positional relationship to the support), a clear spatial positional relationship between the support or a coordinate system of the support and the inertial measurement unit or a coordinate system of the inertial measurement unit may be determined. For this, the inertial measurement unit may be arranged, for example, on the support. In one embodiment, however, the support is moved for the registration, while the target object with the inertial measurement unit arranged thereon is already situated on the support in the position in which subsequently the image data is recorded or should be recorded. The inertial measurement unit is thus moved by the pre-determined motion of the support, where corresponding motion data is recorded by the inertial measurement unit itself. The imaging device (e.g., a data acquisition or data processing facility) may then allocate the motion of the support and the corresponding motion measured thereby by the inertial measurement unit to one another and so carry out or support the registration.

For a motion compensation of translational motion portions or components without taking account of rotational motion portions or components, it may be sufficient to determine the orientation of the inertial measurement unit without determining a position of the inertial measurement unit exactly. If the rotational motion portion is also to be compensated for, then in addition to the orientation, the position of the inertial measurement unit may be determined, for example, from the acquired image data. Further details are given below.

In one embodiment, the motion of the support may be carried out multiple times and/or by an intrinsic motion or a plurality of intrinsic motion cycles (e.g., during a breathing motion or over a plurality of breathing cycles of the target object). This enables the corresponding intrinsic motion or respiratory motion of the target object to be calculated out of the overall motion recorded or measured by the inertial measurement unit. The overall motion recorded by the inertial measurement unit may thus represent a combination or overlaying of the motion of the support brought about by the drive and the intrinsic motion of the target object, whereby the allocation or registration between the coordinate systems of the inertial measurement unit and the imaging device may be falsified. This problem may be circumvented by the development suggested here.

In a further embodiment, the imaging device is configured, for the registration in the image data, to recognize or identify a pre-determined object (e.g., X-ray visible object) automatically. This object may be the inertial measurement unit itself, and/or at least one marker (e.g., X-ray visible marker) arranged in a pre-determined spatial positional relationship to the inertial measurement unit. A position of the inertial measurement unit may thus be determined automatically from the image data directly or indirectly. This position of the inertial measurement unit in the image data and thus in the coordinate system of the imaging device may then be correlated with position or motion data recorded or measured by the inertial measurement unit at a recording time point of the corresponding image data in order to carry out or support the registration.

This process may be advantageous if the inertial measurement unit is already situated in a viewing or recording field of the imaging device. The registration may then be determined or carried out from the image data recorded in any event for imaging the target object, so that, for example, the target object is not subjected to an additional radiation burden. In order to determine the position of the object for the registration, for example, at least two projection images may be recorded as the image data from different angles or with different angulations (e.g., in an epipolar geometry). Equally, using a corresponding design of the inertial measurement unit and/or using a corresponding design and arrangement of the at least one marker, the posture of the inertial measurement unit may be determined from a single projection image. For example, the posture of the inertial measurement unit may be determined repeatedly multiple times during the recording of the image data for imaging the target object (e.g., during a 3D run for recording a 3D CT image data record), for example, based on a plurality or each projection image recorded thereby. By this, a sensor drift of sensors of the inertial measurement unit may be recognized and possibly trapped or compensated for. In addition, a temporal smoothing over a plurality of postures determined one after another (e.g., over different projection images recorded one after another) may be carried out automatically in order to achieve an improved accuracy.

For example, the inertial measurement unit may be arranged in or on a head of a flexible endoscope or another object or instrument used for supporting the target object. In addition, a plurality of, for example, X-ray visible markers may be rigidly arranged in a pre-determined arrangement thereon. An orientation and arrangement of the markers respectively in one or more of the projection images then enables a respective position and alignment of the inertial measurement unit to be determined. Given a sufficient number and/or corresponding arrangement of the marker(s), all six spatial degrees of freedom may then be determined based on the projection image(s) (e.g., specifically, three spatial position coordinates x, y, z and three rotation angles φ, ν, ω). From the projection images, the position and orientation of the endoscope head may then be determined during the 3D run. The motion and possibly rotation of the inertial measurement unit itself and thus also of the endoscope head thereby determined (e.g., recorded or measured simultaneously by the inertial measurement unit) may then be used as the basis for the motion correction or motion compensation in the 3D reconstruction of the CT volume image from the X-ray image data recorded during the 3D run.

For an image quality improved by the motion compensation, it may already be sufficient to determine exactly the position of the inertial measurement unit or of the corresponding device or instrument and/or organ or part of the target object to approximately 2 cm accuracy. For the orientation or angular position, an accuracy of approximately 3° may suffice. Both values are achievable by currently available technology. If, for example, only a motion compensation of the translational motion components (e.g., without taking account of rotational motion components) is to take place, then the position of the inertial measurement unit does not have to be determined or only to, for example, 10 cm accuracy.

In a further embodiment, the imaging device includes a wire along which at least one, for example, X-ray visible marker is arranged. The or an inertial measurement unit is respectively arranged in or on the at least one marker. Thus, a dedicated inertial measurement unit is arranged in or on each, some, or one of the markers. The wire is connected to the respective inertial measurement unit as a data connection for transferring the motion data thereof. The at least one inertial measurement unit is thus connected via the wire functioning as the data connection to a corresponding interface of the data connection or data processing facility of the imaging device. The marker(s) may be firmly connected or coupled to the wire or may be movable along the wire and possibly fixable. The at least one marker may be used, for example, for marking a respective position of an anatomical feature (e.g., a lesion). The measurement or motion data transferred from the at least one inertial measurement unit may then be used, for example, to localize the at least one marker more easily during a procedure or intervention (e.g., automatically).

In other words, the imaging device may be moved or controlled automatically dependent upon the position or motion data transferred by the at least one inertial measurement unit in order to align a field of view or a recording region of the imaging device for the image data such that the position of the at least one marker is contained within the field of view or recording region. The imaging device may thus be configured for a corresponding automatic control or alignment.

Through the use of the wire as a data connection, an additional or separate data connection may be saved, and thereby, a use may be simplified. In addition, the wire-bound transfer of the motion data is particularly reliable and relatively unsusceptible to faults, for example, in contrast to a wireless (e.g., radio-based) transfer. In addition, on use of the wire as a data connection, the inertial measurement unit may be particularly compactly constructed, whereby the inertial measurement unit is usable particularly flexibly and with a particularly low burden for the respective patient.

In a further embodiment, the imaging device is configured to acquire as the image data fluoroscopy data or fluoroscopy images of the target object simultaneously with the motion data. The imaging device is configured to determine a respiration curve of the target object from the fluoroscopy data and thus to correlate the motion data for the registration. Since an orientation or posture of the target object is pre-determined by arrangement for an imaging by the imaging device, dependent upon the anatomy, a motion direction of the target object is also pre-determined by the breathing or during the breathing (e.g., in the coordinate system of the imaging device or the image data). This motion direction may then be brought through corresponding temporal allocation or correlation into agreement with a motion or motion direction recorded or acquired by the inertial measurement unit as part of the motion data, whereby the registration may be carried out or supported. The fluoroscopy data may thereby be, for example, such fluoroscopy data that is in any event recorded or to be recorded for imaging (e.g., for examining the target object). Using the procedure proposed here, therefore, an additional radiation burden on the target object for the registration may also be prevented.

In a further embodiment, the inertial measurement unit includes at least one acceleration sensor. The imaging device is then configured to acquire the image data and simultaneously the motion data during a cyclical motion (e.g., during a respiratory motion of the target object) to determine a respective phase (e.g., a breathing phase) of the cyclical motion based on the motion data, and to carry out the motion compensation based on the respectively determined phase. Thus, in other words, a motion cycle of the target object is recorded in an image-based manner together with the associated motion or acceleration signal of the inertial measurement unit.

The acceleration signal of the inertial measurement unit is then used to determine the respective current portion of the motion or respiratory cycle. Thereby, an image rate or recording rate of the image data may be reduced. This applies both for a learning of the motion or respiratory cycle as well as for a subsequent recording of further image data, for example, with or during the use of the aforementioned motion-compensated overlay image. Since by using a pre-determined orientation or arrangement of the target object, a motion direction during the cyclical motion is at least roughly pre-determined and is thus known; in this way, the motion compensation may be carried out particularly easily and reliably. Since the motion data may be continuously recorded by the inertial measurement unit, no assumption is to be made regarding a regularity or evenness of the cyclical motion for the motion compensation. The present embodiments thus advantageously enable a particularly accurate motion compensation and thus an improved image quality.

In a further embodiment, the inertial measurement unit includes at least one magnetic field sensor and is configured to measure an intensity or a gradient and/or a direction (e.g., a spatial structure of a respective local magnetic field). The imaging device thereby includes a magnetic field generator and, using this magnetic field generator, is configured to generate in the region of the inertial measurement unit, a magnetic field with a pre-determined spatial structure relative to the coordinate system of the image data or the at least one image generated therefrom. The spatial structure may specify a direction of the magnetic field (e.g., the magnetic field lines), and/or a direction of a gradient of a field intensity, and/or a spatial distribution of the field intensity of the magnetic field intensity. Alternatively, the spatial structure may be determined or characterized thereby. The imaging device is then further configured to determine, for the registration, the posture of the inertial measurement unit from the intensity and/or direction of the generated magnetic field measured thereby.

Additionally or alternatively, the magnetic field may be generated sequentially from a plurality of directions or in different arrangements or alignments and is respectively measured by the inertial measurement unit in order to achieve an improved accuracy. Since the magnetic field may permeate or penetrate many materials (e.g., electrically non-conductive materials), in contrast to the use of optically tracked markers, it is not necessary that the inertial measurement unit or a marker coupled thereto must be located in a visual field or field of view of an optical camera. In contrast to ionizing radiation, the magnetic field advantageously causes no damage to the target object.

In a further embodiment, the imaging device is also configured to acquire ECG data of the target object and/or a respiration curve of a ventilation machine supplying the target object, and to generate the motion-compensated image or video. The imaging device is configured to merge (e.g., combine) the motion data with the ECG data and/or with the respiration curve. Using the ECG data and/or the respiration curve, a respective boundary condition is pre-determined for the motion compensation. In other words, the imaging device is thus configured to carry out a fusion of measurement or sensor data from different sources.

The ECG data and/or the respiration curve pre-determined by the ventilation machine form, together with the motion data, a broader database whereby an accuracy and reliability or confidence of the motion compensation may be improved. This is attributable, for example, to all of these variables or data possibly being error-laden, despite these errors or measurement inaccuracies being independent of one another. In addition, the ECG data and/or the respiration curve serve, for example, as a reference for the motion data in order to recognize a sensor drift of sensors of the inertial measurement unit and possibly to balance the sensor drift out or trap the sensor drift. For example, the ECG data and/or the respiration curve may specify a periodicity for the motion data.

In order to merge or combine the ECG data and/or the respiration curve with the motion data, in the simplest case, for example, from all the different data types, a respective motion of the target object is determined, and subsequently, a mean motion of the target object may be determined therefrom and used for the motion compensation.

Even if not explicitly described here, the present embodiments may also be used for subtraction modes (e.g., for a roadmap method or a digital subtraction angiography (DSA)), possibly in conjunction with the already known methods. Some or all of the embodiments, developments, measures, or procedures described may be combined with one another, for example, for a further improved accuracy of the registration.

A further aspect of the present embodiments is a method for generating a motion-compensated image or video. In the method, using a data acquisition facility, image data of a target object is acquired. For example, if the image data is, for example, X-ray image data or MR image data, using a reconstruction facility (e.g., including one or more processors), at least one X-ray image or MR image of the target object may be generated from this X-ray or MR image data. According to the present embodiments, it is provided that in the method using a registration facility, a posture of an inertial measurement unit is acquired, and, on the basis thereof, a registration between coordinate systems of the inertial measurement unit and the image data or at least one image generated therefrom is carried out. Motion data is acquired from the inertial measurement unit arranged on the target object. The motion-compensated image or video is then generated automatically while processing at least the motion data. The method may thus be understood as a method for operating the imaging device according to the present embodiments. Accordingly, the facilities and devices mentioned in relation to the method may be, for example, the facilities and devices already mentioned in relation to the imaging device according to the present embodiments. Some or all of the measures or procedures described in connection with the other aspects (e.g., in connection with the imaging device) may be provided as further method acts of the method according to the present embodiments.

The method may be a computer-implemented method. Accordingly, a further aspect of the present embodiments is a computer program product or computer program that includes commands or control instructions that, when the imaging device executes the computer program product or computer program, cause the imaging device to carry out at least one embodiment of the method.

A further aspect of the present embodiments is a computer-readable storage medium (e.g., a non-transitory computer-readable storage medium) on which at least one embodiment of the computer program product is stored. In addition, further commands, further control instructions, or further program code may be stored on the computer-readable storage medium.

In a further embodiment, using the inertial measurement unit and/or through tracking of markers and/or possibly simultaneous fluoroscopy, the motion or motion trajectory of the target object may be recorded, for example, during at least one respiratory cycle. During the recording of the image data for imaging the target object, the motion or motion trajectory thereby determined may then be added onto a motion of the imaging device (e.g., a C-arm). Thereby, the imaging device or at least one image recording facility of the imaging device moves with the target object, so that the imaging device or an image recording facility of the imaging device and the target object are at rest relative to one another except for the relative motion of the imaging device or the image recording facility necessary for recording the image data. The imaging device or the image recording facility of the imaging device thus then reproduces the respiratory motion of the target object, whereby this motion is effectively compensated for and thus does not lead to a blurring or an unsharpness in a reconstructed image or a live image (e.g., a live X-ray image). This procedure (e.g., the motion of hardware) may be provided in addition to the other described measures that may be carried out in software. The software motion compensation may thus additionally be carried out in order, for example, to correct or prevent motion artifacts still remaining from an inaccuracy or inertia in the control of the imaging device.

The imaging device according to the present embodiments may include, for example, as part of the mentioned facilities, a computer-readable storage medium according to the present embodiments. For carrying out the computer program or program code stored on the computer-readable storage medium, the imaging device may include at least one processor device (e.g., a microprocessor or a microcontroller) that is connected or coupled to the computer-readable storage medium by a data connection.

The features, embodiments, and/or processes described above for, or in connection with, an X-ray imaging may accordingly apply and be used (e.g., correspondingly transferred) for other imaging methods (e.g., ultrasound, magnetic resonance imaging, endoscopy, or video imaging or the like).

The properties and developments of the imaging system of the present embodiments and the method of the present embodiments set out above and in the following, as well as the corresponding advantages are each analogously and reciprocally transferable between these and equally the other aspects of the present embodiments (e.g., therefore, to the computer program product and the computer-readable storage medium of the present embodiments, and vice versa). Such developments of the imaging device, the method, the computer program product, and the computer-readable storage medium, which have embodiments that, for the avoidance of unnecessary redundancy, are not explicitly described here in the respective combination or are not separately described for each of these aspects of the present embodiments, thus also belong to the invention.

DETAILED DESCRIPTION

Components of the embodiments as described in the exemplary embodiments each represent individual features that are to be regarded as independent of one another. The components of the embodiments each also further develop the invention independently of one another and are thus also to be considered individually, or in a different combination from that shown, as part of the invention. The embodiments described are also enhanceable through others of the previously described features of the invention.

Figure 1:
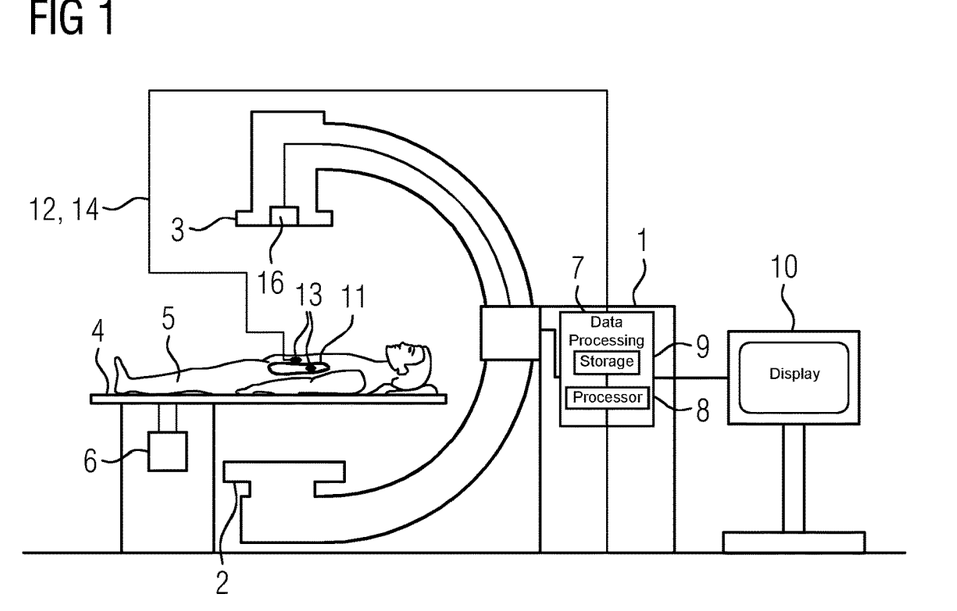
FIG. 1 shows a schematic side view of one embodiment of an imaging device.

FIG. 1 shows a schematic side view of one embodiment of an imaging device 1 with a radiation source 2 and a detector 3. In the present case, the imaging device 1 is configured as an X-ray device. The examples described below apply equally, however, for other types of imaging devices (e.g., a magnetic resonance (MR) or ultrasonic device or an endoscope). The form shown as a C-arm device is purely exemplary and schematic. For example, the imaging device 1 may be configured, for example, as a computed tomography device. Arranged in the present case between the radiation source 2 and the detector 3 is a patient table 4, on which a patient 5 who is to be examined or imaged is arranged. The patient table 4 has a drive 6, by which the patient table 4 is movable or displaceable. Using the drive 6, therefore, in the present example, the patient table 4 and therewith the patient 5 may be displaced or moved back and forth relative to the radiation source 2 and the detector 3 in different spatial directions.

In the present case, the imaging device 1 includes a data processing facility 7 indicated in FIG. 1 purely schematically with a computer-readable storage medium 8 and a processor device 9 connected thereto. Stored on the storage medium 8 is a computer program or program code that encodes or represents a method for operating the imaging device for generating a motion-compensated image or video of the patient 5 or a subregion of the patient 5. This computer program or this program code is executable by the processor device 9 for carrying out the method.

Also shown is a display device 10 (e.g., a screen or monitor) connected to the data processing facility 7. The display device 10 may be part of the imaging device 1 or connected thereto. The motion-compensated image or video generated may be displayed on the display device 10.

Figure 2:
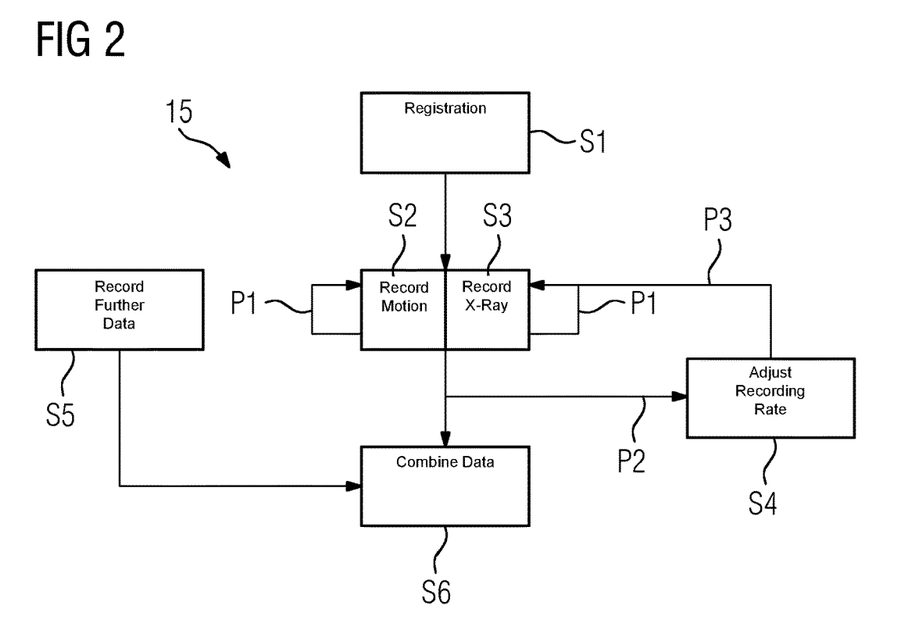
FIG. 2 shows an exemplary schematic flow diagram of one embodiment of a method for generating a motion-compensated image or video of a target object.

FIG. 2 shows, by way of example, a schematic flow diagram 15 for a corresponding method for generating the motion-compensated image or video using the imaging device 1. This method or the flow diagram 15 will now be described in greater detail making reference to FIG. 1.

For example, in computed tomography (CT) recordings, due to a respiratory motion, anatomical structures in the abdomen often become blurred, which may make reconstructed recordings or images diagnostically unusable. For example, for recordings of the liver or the gall duct, a motion compensation would be desirable to improve the quality of the resulting recordings or images. Added thereto as a complicating factor is that patients are often only lightly sedated and are not actively ventilated so that a reliable control of the respiratory motion is practically impossible.

For example, in the case of interventional CT recordings of the liver or the biliary tract, typically an access by an instrument 12 such as, for example, a catheter or a flexible endoscope is provided, by which an X-ray visible marker and/or a sensor may be introduced into or onto an organ 11 of the patient 5 that is to be imaged. Thereby, a motion of the organ 11 caused by the breathing and/or a heartbeat or another intrinsic motion of the patient 5 may be directly measured, in effect "from the inside out".

In the present case, a catheter with an integrated inertial measurement unit 13 (IMU) is introduced into or onto the organ 11 by the instrument 12. The catheter may be left, for example, close to a head of the instrument 12, or introduced into a biliary duct. In one embodiment, the catheter has only a small proportion of metal to avoid image artifacts. The or a further inertial measurement unit 13 may also be arranged or integrated in or on the head of the instrument 12.

In one embodiment, X-ray visible markers or marking points are arranged on the catheter (e.g., close to the inertial measurement unit 13 and/or on the inertial measurement unit 13, and/or the inertial measurement unit 13 itself is X-ray visibly designed) and may thus be used as an X-ray visible marker or marking point.

In one embodiment, a plurality of inertial measurement units 13 may be present or arranged along the catheter or along the instrument 12, so that a motion of the organ 11 may be measured at a plurality of sites. In this case, for example, a non-rigid motion of the organ 11 may be modeled with a biomechanical model of the organ 11 and/or by spatial interpolation. For example, in image-guided video assisted thoracoscopic surgery (iVATS), sometimes markers ("fiducials") are used for marking lesions. These markers are fastened to a wire 14 (also shown only schematically here) that extends along a needle path out of the patient 5 or away from the patient 5. In the present case, further inertial measurement units 13 are integrated in these markers. In the present case for the sake of clarity, only one of these further inertial measurement units 13 is shown on a surface of the organ 11. The wire 14 is connected, at one end facing away from the patient 5, to the data processing facility 7 and serves herein as a data connection for transferring measurement or sensor data of the inertial measurement units 13 to the data processing facility 7. By using this scan or sensor data that is recorded and provided by the inertial measurement unit 13, the respective locations of the markers may be more easily localized during a procedure, an intervention, or operation.

In the present case, using the inertial measurement unit 13 during a 3D run (e.g., during a recording of a 3D CT data record of the patient 5 or the organ 11), a local motion of the organ 11 occurring thereby is measured. Since the inertial measurement units 13 are arranged in or on the organ 11, the inertial measurement units 13 follow the motion of the organ 11. Based on motion data accordingly recorded by the inertial measurement units 13, in the event of an image creation or image reconstruction from the 3D CT data record, the motion of the organ 11 is compensated for so that a motion-compensated image or video of the patient 5 or of the organ 11 is created. Equally, the motion data recorded by the inertial measurement units 13 may be used as the basis for a motion-compensated overlay (e.g., a motion-compensated overlay image) since the inertial measurement units 13 perform at least approximately the same motion as the examined organ 11.

Initially, however, the problem exists that the inertial measurement units 13 provide only relative motion data in their own coordinate system, and an absolute motion curve (e.g., a location and an orientation of the inertial measurement units 13 in the coordinate system of the imaging device 1, relative to the radiation source 2 and the detector 3) are initially not known. The challenge therefore exists of determining a registration between the spatial axes of the respective local coordinate system of the inertial measurement units 13 in which the motion (e.g., a translation and/or a rotation) is measured or detected, and the coordinate system of the imaging device (e.g., the X-ray coordinate system).

This registration is carried out in this case in a method act S1. For this purpose, there is a plurality of possibilities that may be used alternatively or in combination with one another.

As a pragmatic solution, the respective spatial orientation of the inertial measurement units 13 may be determined before the 3D run in that the patient table 4 is moved by the drive 6 upwardly and downwardly as well as laterally, and a measurement signal of the inertial measurement units 13 recorded thereby (e.g., corresponding motion data) may be allocated accordingly. The patient table 4 is thus moved automatically or manually in the different spatial directions successively (e.g., with a smallest possible amplitude that may just be detected by the inertial measurement units 13). The motion or a motion or displacement scope for the motion of the patient table 4 is thus specified, for example, dependent upon a sensitivity of the inertial measurement units 13. By multiple execution of the motion, a superposition of a respiratory motion of the patient 5 during the motion or displacement of the patient table 4 may be subtracted out. Alternatively, the respiration may be briefly paused during the motion of the patient table 4. Optionally, these motions of the patient table may be repeated with a relatively small amplitude during the motion correction (e.g., multiple times over and again).

The respective position or the respective location of the inertial measurement units 13 or of the X-ray visible markers situated in their vicinity may be determined, at least approximately, by reconstruction from at least two projections or projection images recorded by the imaging device 1. In one embodiment, particularly high accuracy is not required for the determination of the position or the location in order to achieve a motion correction or motion compensation and thereby, an improved image quality.

Additionally or alternatively, by an image recognition, the position (e.g., the location of the inertial measurement units 13 or the corresponding X-ray visible marker(s)) may be determined in one, some, or all of the recorded projection images. For the location of one of the inertial measurement units 13 in the nth projection image at the time point $t_n$, the following may apply:

$$(x_{IMU,projection\ image}(t_n), y_{IMU,projection\ image}(t_n)) = M_n (x_{IMU}(t_n), y_{IMU}(t_n), z_{IMU}(t_n)),$$

where $M_n$ denotes the projection matrix of the nth projection image. The projection matrix $M_n$ describes how, according to a ray path from the radiation source 2 to the detector 3, a three-dimensional point in the space of the ray path or ray cone to one or more pixels in the respective projection image (e.g., into the 2D plane of the detector 3) is imaged. The inertial measurement unit 13 records a motion curve within its local coordinate system, which may be specified as a tuple $(a(t_n), b(t_n), c(t_n), \alpha(t_n), \beta(t_n), \gamma(t_n))$ with spatial coordinates a, b, c and spatial or rotation angles $\alpha, \beta, \gamma$. An origin is placed at the time zero point $t_0$, so that the following also applies:

$$(a(t_0), b(t_0), c(t_0), \alpha(t_0), \beta(t_n), \gamma(t_n)) = 0.$$

A conversion from the local coordinate system of the inertial measurement unit 13 into the X-ray or world coordinate system x, y, z, $\varphi$, $\nu$, $\omega$ is given by:

$$(x_{IMU}(t_n), y_{IMU}(t_n), z_{IMU}(t_n), \varphi(t_n), \nu(t_n), \omega(t_n)) = R(a(t_n), b(t_n), c(t_n), \alpha(t_n), \beta(t_n), \gamma(t_n), x_{IMU}(t_0), y_{IMU}(t_0), z_{IMU}(t_0), \varphi(t_0), \nu(t_0), \omega(t_0)),$$

with an initially unknown transformation matrix R and unknown coordinates at $t_0$. On use of a sufficient number of projections, a resulting equation system is overdetermined and may be solved numerically by known methods, so that the motion and rotary or rotation curve of the inertial measurement unit 13 may be determined in the world coordinate system.

Therefrom, a motion field, possibly with a rotation component of the organ 11 may now be determined and compensated for in the image reconstruction.

If relevant, with a suitable selection of the coordinate systems and/or corresponding starting points and/or parameters, the calculation may be simplified to:

$$(x_{IMU}(t_n), y_{IMU}(t_n), z_{IMU}(t_n), \varphi(t_n), \nu(t_n), \omega(t_n)) = R(a(t_n), b(t_n), c(t_n), \alpha(t_n), \beta(t_n), \gamma(t_n)) + (x_{IMU}(t_0), y_{IMU}(t_0), z_{IMU}(t_0), \varphi(t_0), \nu(t_0), \omega(t_0)).$$

Equally, the imaging device 1 may be configured for carrying out a fluoroscopy (e.g., for recording fluoroscopy data or fluoroscopy images of the patient 5 or the organ 11). Then, using fluoroscopy, respiratory motions may be recorded from one or more angulations with the imaging device 1, and the motion curve meanwhile measured by the inertial measurement unit 13 may be correlated thereto. In one embodiment, an excessively high frame or recording rate is thereby not necessary, as would be needed for a fluid video representation, and a complete respiratory cycle also does not necessarily have to be recorded.

The registration of the inertial measurement unit 13 within an image plane of the projection images according to the coordinates x, y, z may be derived by a detection of an X-ray visible object of, for example, the inertial measurement units 13 themselves and/or of the aforementioned X-ray visible markers in the fluoroscopy data or fluoroscopy images. If no such registration is present, the aforementioned overlay or overlay image may be moved or co-moved, for example, globally according to the motions detected by the inertial measurement units 13.

Equally, the registration may additionally or alternatively take place or be supported via a magnetic field. For this, herein the imaging device 1 has a magnetic field generator 16 for generating a magnetic field with a pre-determined structure in the region of the inertial measurement units 13. Using the magnetic field generator 16, therefore, an external magnetic field may be applied or generated, possibly successively from a plurality of directions. This magnetic field is then detected spatially (e.g., with regard to its direction, intensity, and/or its gradient) by corresponding magnetic field sensors of the inertial measurement units 13. Using an allocation between the pre-determined structure of the magnetic field, according to generation by the magnetic field generator 16 and the magnetic field generated by the inertial measurement units 13, the registration is then possible.

During the actual examination or imaging of the patient 5 or the organ 11, in a method act S2, the motion curve, thus corresponding motion data, is recorded or registered by the inertial measurement units 13, which is schematically indicated in the present case by a loop-like program path P1. In parallel therewith, to image the patient 5 or the organ 11 in a method act S3, X-ray data (e.g., projection images or the 3D CT data record) is recorded by the imaging device 1.

Thereby, a plurality of individual projection images may be recorded sequentially, which herein is also schematically indicated by the loop-like program path P1. In one embodiment, herein, using continued recognition of the position of the inertial measurement unit 13 in the recorded X-ray image data (e.g., in the recorded 2D projection images and by adjustment with the motion data measured by the inertial measurement units 13), the registration of the spatial axes of the coordinate system or the coordinate systems of the inertial measurement units 13 are continuously checked and/or updated with the X-ray coordinate system.

Depending on the application case, at least temporarily during the method act S3 (e.g., during the 3D run and/or during the fluoroscopy navigation), the recording rate of the X-ray image records (e.g., the fluoroscopy or projection images) may be automatically reduced and/or increased adaptively. This is shown schematically by a program path P2 and a method act S4, in which the respective adaptation or adjustment of the recording rate is carried out, and a program path P3 is schematically indicated.

In general, one of the inertial measurement units 13 in each case may have sufficiently many acceleration and rotation or pivot rate sensors, so that motions and rotations in all the spatial directions and all the spatial axes may be detected. Equally, however, it is possible, for example, for cost and/or space reasons to use a simplified inertial measurement unit 13 that may measure, for example, an acceleration just in one or two spatial directions. In such a case also, the corresponding motion or acceleration data may be used for a motion compensation and thus finally for an improved image quality. For this, this motion data may be combined, for example, with an image-based recording or determination of a motion cycle of the patient 5.

In parallel therewith, further data (e.g., an ECG signal and/or a respiration curve and/or the like) may be recorded in a method act S5.

In a method act S6, the available data (e.g., the X-ray image data, the motion data and possibly the further data) may be combined with one another in order to generate the motion-compensated or motion-corrected image or video. The motion compensation of the aforementioned overlay may take place, for example, in the case of a compensation of heart motions using a combination of the motion data from the inertial measurement units 13 and the ECG data.

The motion-compensated image generated in the method act S6 may be, for example, a motion-compensated CT volume image or the aforementioned motion-compensated overlay. The overlay may be or include, for example, a virtual object or model, for example, of the catheter or the instrument 12 and/or the organ 11 and, for example, may be overlaid motion-compensated on an X-ray or projection image or a laparoscopy video.

The flow diagram 15 should be understood as purely schematic. The aforementioned method acts S1 to S6 may thus stand or be carried out in different temporal relations to one another (e.g., temporally overlapping or sequential to one another). The method acts S1 to S6 and the program paths P1 to P3 may be or represent program modules, functional blocks, or functions of a computer program that encodes the method described here (e.g., may initiate or bring about execution).

The examples described show how, by using an inertial measurement unit 13, a motion compensation may be used, for example, for CT recordings or for an overlay (e.g., an overlay image) in order to achieve or enable an improved image quality (e.g., without an additional radiation burden for the patients 5).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An imaging device for generating a motion-compensated image or video, the imaging device comprising:
   a data acquisition facility configured to acquire image data of a target object,
   wherein the imaging device is configured to:
      acquire, by a registration facility, a posture of an inertial measurement unit;
      carry out a registration between coordinate systems of the inertial measurement unit and the image data or an image generated from the image data based on the acquired posture of the inertial measurement unit;
      acquire motion data from the inertial measurement unit arranged on the target object; and
      generate the motion-compensated image or video, the generation of the motion-compensated image or video comprising processing of the acquired motion data.

2. The imaging device of claim 1, wherein the data acquisition facility is configured to acquire a three-dimensional (3D) computed tomography (CT) data record as the image data, and
   wherein the imaging device is further configured to:
      acquire the motion data of the inertial measurement unit simultaneously with the acquisition of the 3D CT data record; and
      reconstruct, from the 3D CT data record and the acquired motion data, a motion-compensated 3D image of the target object as the motion-compensated image.

3. The imaging device of claim 1, wherein the generation of the motion-compensated image or video comprises generation of a motion-compensated overlay image from the acquired motion data of the inertial measurement unit, and
   wherein the imaging device is further configured to overlay the motion-compensated overlay image on the image data or the image generated from the image data.

4. The imaging device of claim 3, wherein the imaging device is further configured to, during acquisition of the motion data, automatically reduce a recording rate at which the imaging device acquires the image data to a pre-determined value or automatically reduce the recording rate at which the imaging device acquires the image data by the pre-determined value.

5. The imaging device of claim 3, wherein the imaging device is further configured to:
   regularly and repeatedly acquire the image data;
   automatically detect, based on a contrast of the image data or the image generated from the image data, a contrast medium injection; and automatically increase a recording rate for the image data to a pre-determined value when the contrast medium injection is detected or automatically increase the recording rate for the image data by the pre-determined value when the contrast medium injection is detected.

6. The imaging device of claim 1, further comprising a movably mounted support equipped with a drive for arranging the target object on the movable mounted support,
wherein the imaging device is configured, on a motion of the movably mounted support in different spatial directions, to place the motion and the motion data of the inertial measurement unit in relation to one another, such that the posture or an orientation of the inertial measurement unit is determined.

7. The imaging device of claim 1, wherein the imaging device is further configured, for the registration in the image data, to automatically recognize a pre-determined object in the image data,
wherein the object is the inertial measurement unit, at least one marker arranged in a pre-determined positional relationship relative to the inertial measurement unit, or the inertial measurement unit and the at least one marker.

8. The imaging device of claim 1, further comprising a wire along which at least one X-ray visible marker is arranged,
wherein the inertial measurement unit is arranged in or on the at least one X-ray visible marker, and the wire is connected to the inertial measurement unit as a data connection for transferring the motion data of the inertial measurement unit.

9. The imaging device of claim 1, wherein the imaging device is further configured to:
acquire, as the image data, fluoroscopy data of the target object simultaneously with the motion data;
determine a respiration curve of the target object the fluoroscopy data; and
correlate the motion data for the registration.

10. The imaging device of claim 1, wherein the inertial measurement unit comprises at least one acceleration sensor, wherein the imaging device is configured to acquire the image data and simultaneously the motion data during a cyclical motion, and
wherein the imaging device is further configured to:
determine a respective phase of the cyclical motion based on the motion data; and
carry out the motion compensation based on the respectively determined phase.

11. The imaging device of claim 10, wherein the cyclical motion is a respiratory motion of the target object, and the phase is a breathing phase.

12. The imaging device of claim 1, wherein the inertial measurement unit comprises at least one magnetic field sensor and is configured to measure an intensity, direction, or intensity and direction of a respective local magnetic field, and
wherein the imaging device comprises a magnetic field generator and is further configured to:
generate, by the magnetic field generator, in a region of the inertial measurement unit, a magnetic field with a pre-determined spatial structure relative to the coordinate system of the image data; and
determine for the registration, the posture of the inertial measurement unit from the measured intensity, direction, or intensity and direction of the generated magnetic field.

13. The imaging device of claim 1, wherein the imaging device is further configured to acquire echocardiogram (ECG) data of the target object, a respiration curve of a ventilation machine supplying the target object, or the ECG data of the target object and the respiration curve of the ventilation machine supplying the target object,
wherein generation of the motion-compensated image or video comprises merging of the motion data with the ECG data, the respiration curve, or the ECG data and the respiration curve, and
wherein, through the ECG data, the respiration curve, or the ECG data and the respiration curve, a respective boundary condition is pre-determined.

14. A method for generating a motion-compensated image or video, the method comprising:
acquiring, by a data acquisition facility, image data of a target object;
acquiring, by a registration facility, a posture of an inertial measurement unit;
carrying out a registration between coordinate systems of the inertial measurement unit and the image data or an image generated from the image data, respectively, based on the acquired posture of the inertial measurement unit;
acquiring motion data from the inertial measurement unit arranged on the target object; and
automatically generating the motion-compensated image or video while processing at least the motion data.

15. In a non-transitory computer-readable storage medium that stores instructions executable by one or more processors to generate a motion-compensated image or video, the instructions comprising:
acquiring, by a data acquisition facility, image data of a target object;
acquiring, by a registration facility, a posture of an inertial measurement unit;
carrying out a registration between coordinate systems of the inertial measurement unit and the image data or an image generated from the image data, respectively, based on the acquired posture of the inertial measurement unit;
acquiring motion data from the inertial measurement unit arranged on the target object; and
automatically generating the motion-compensated image or video while processing at least the motion data.

* * * * *